US012576533B2

(12) United States Patent
Hourtash

(10) Patent No.: US 12,576,533 B2
(45) Date of Patent: Mar. 17, 2026

(54) TECHNIQUES FOR FOLLOWING COMMANDS OF AN INPUT DEVICE USING A CONSTRAINED PROXY

(71) Applicant: INTUITIVE SURGICAL OPERATIONS, INC., Sunnyvale, CA (US)

(72) Inventor: Arjang M. Hourtash, Millbrae, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 143 days.

(21) Appl. No.: 18/683,630

(22) PCT Filed: Aug. 17, 2022

(86) PCT No.: PCT/US2022/040644
§ 371 (c)(1),
(2) Date: Feb. 14, 2024

(87) PCT Pub. No.: WO2023/023186
PCT Pub. Date: Feb. 23, 2023

(65) Prior Publication Data
US 2024/0375282 A1 Nov. 14, 2024

Related U.S. Application Data

(60) Provisional application No. 63/234,645, filed on Aug. 18, 2021.

(51) Int. Cl.
*B25J 9/16* (2006.01)
*A61B 34/00* (2016.01)
(Continued)

(52) U.S. Cl.
CPC ............. *B25J 9/1689* (2013.01); *A61B 34/35* (2016.02)

(58) Field of Classification Search
CPC ........ B25J 9/1689; A61B 34/35; A61B 34/37; A61B 34/77; G05B 2219/40117; G05B 2219/40118; G05B 2219/40195
(Continued)

(56) References Cited

U.S. PATENT DOCUMENTS 5,053,976 A * 10/1991 Nose ...................... B25J 9/1607
901/3
5,454,827 A * 10/1995 Aust .................... A61B 1/0052
606/174
(Continued)

FOREIGN PATENT DOCUMENTS

WO WO-2013122889 A1 8/2013
WO WO-2018005636 A1 1/2018
WO WO-2018013187 A1 1/2018

OTHER PUBLICATIONS

International Search Report and Written Opinion for Application No. PCT/US2022/40644, mailed Jan. 24, 2023, 26 pages.
(Continued)

*Primary Examiner* — Jaime Figueroa
(74) *Attorney, Agent, or Firm* — Artegis Law Group, LLP

(57) ABSTRACT

Disclosed techniques include a computer-assisted device having an input control, a functional structure, and a processing system. The functional structure is configured to include a repositionable structure, and the repositionable structure is configured to support an instrument. The processing system is configured to receive a movement command from the input control, update a pose of a proxy based on the movement command and a proxy constraint, and cause the functional structure to move based on the updated pose of the proxy. In some embodiments, the input control
(Continued)

controls a pose of a virtual leader device. The processing system updates a pose of a proxy based on the pose of the virtual leader device, updates a pose of a virtual follower device based on the updated pose of the proxy, and causes the functional structure to move based on the pose of the virtual follower device.

20 Claims, 7 Drawing Sheets

(51) Int. Cl.
  *A61B 34/35* (2016.01)
  *A61B 34/37* (2016.01)
(58) Field of Classification Search
  USPC ................. 700/245–264; 318/568.11–568.25
  See application file for complete search history.

(56) References Cited

U.S. PATENT DOCUMENTS

| | | | | |
|---|---|---|---|---|
| 5,631,973 | A * | 5/1997 | Green | H04N 13/337 |
| | | | | 382/128 |
| 5,737,500 | A * | 4/1998 | Seraji | B25J 9/1643 |
| | | | | 700/262 |
| 5,808,665 | A * | 9/1998 | Green | H04N 13/337 |
| | | | | 348/E13.016 |
| 5,938,678 | A * | 8/1999 | Zirps | A61B 17/29 |
| | | | | 606/174 |
| 6,331,181 | B1 * | 12/2001 | Tierney | G16H 40/63 |
| | | | | 606/130 |
| 6,394,998 | B1 * | 5/2002 | Wallace | A61B 34/35 |
| | | | | 901/29 |
| 6,424,885 | B1 * | 7/2002 | Niemeyer | A61B 34/77 |
| | | | | 600/109 |
| 6,671,581 | B2 * | 12/2003 | Niemeyer | A61B 34/37 |
| | | | | 600/109 |
| 11,625,107 | B2 * | 4/2023 | Tabandeh | A61B 34/37 |
| | | | | 606/19 |
| 2004/0039485 | A1 | 2/2004 | Niemeyer et al. | |
| 2019/0105117 | A1 | 4/2019 | Brisson | |
| 2019/0254763 | A1 | 8/2019 | Lambrecht et al. | |
| 2020/0409477 | A1 * | 12/2020 | Tabandeh | B25J 13/025 |
| 2023/0263585 | A1 | 8/2023 | Hourtash et al. | |

OTHER PUBLICATIONS

Mitra, P. "Model Mediation for Time-Delayed teleoperation," ProQuest LLC, Sep. 2008, 167 pages.
Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

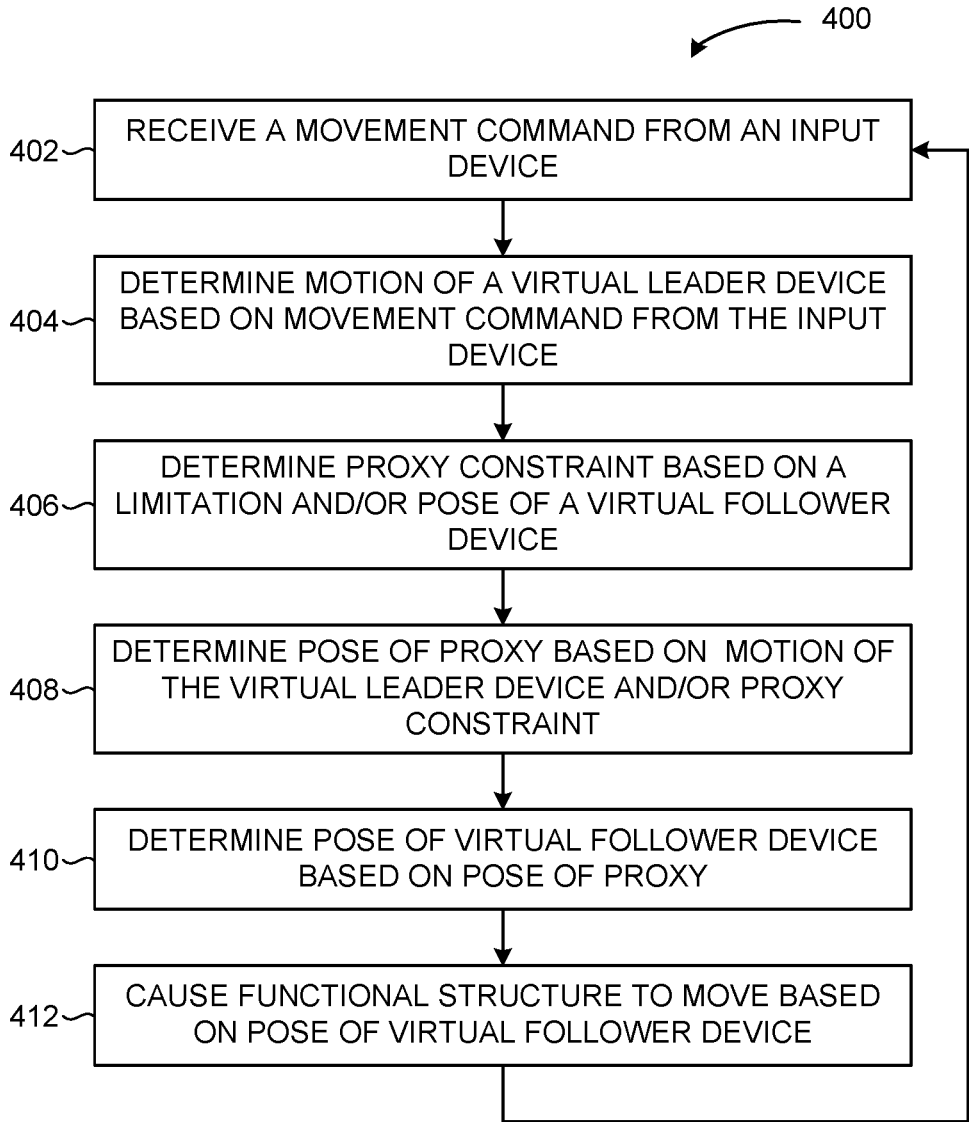

_400_

402 — RECEIVE A MOVEMENT COMMAND FROM AN INPUT DEVICE

404 — DETERMINE MOTION OF A VIRTUAL LEADER DEVICE BASED ON MOVEMENT COMMAND FROM THE INPUT DEVICE

406 — DETERMINE PROXY CONSTRAINT BASED ON A LIMITATION AND/OR POSE OF A VIRTUAL FOLLOWER DEVICE

408 — DETERMINE POSE OF PROXY BASED ON MOTION OF THE VIRTUAL LEADER DEVICE AND/OR PROXY CONSTRAINT

410 — DETERMINE POSE OF VIRTUAL FOLLOWER DEVICE BASED ON POSE OF PROXY

412 — CAUSE FUNCTIONAL STRUCTURE TO MOVE BASED ON POSE OF VIRTUAL FOLLOWER DEVICE

_FIGURE 4_

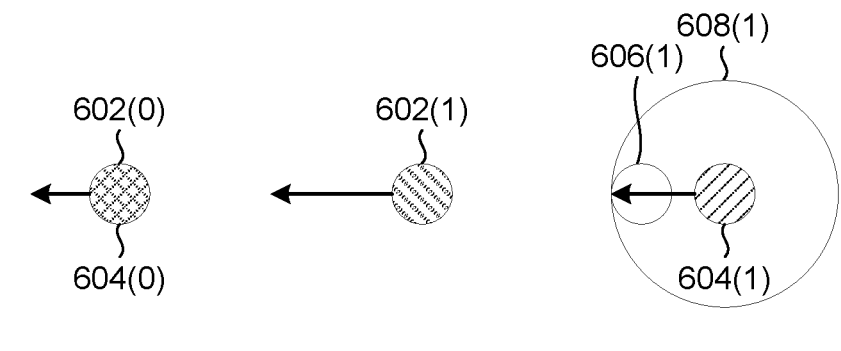
*FIGURE 6A*        *FIGURE 6B*
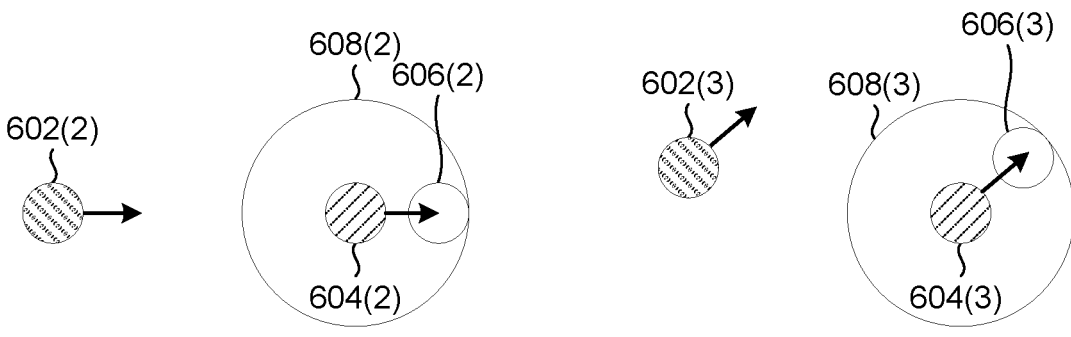
*FIGURE 6C*        *FIGURE 6D*
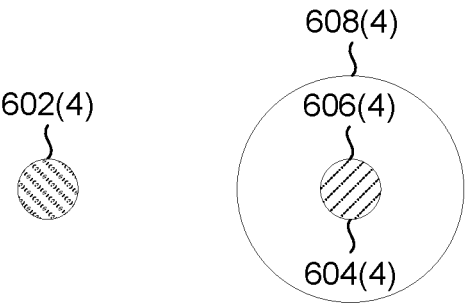
*FIGURE 6E*

TECHNIQUES FOR FOLLOWING COMMANDS OF AN INPUT DEVICE USING A CONSTRAINED PROXY

RELATED APPLICATIONS

This application is a U.S. National Stage patent application of International Patent Application No. PCT/US2022/040644, filed Aug. 17, 2022, and claims the benefit to U.S. Provisional Application No. 63/234,645, filed Aug. 18, 2021, and entitled "Techniques for Following Commands of an Input Device using a Constrained Proxy," each of these related applications is incorporated by reference herein.

TECHNICAL FIELD

The present disclosure relates generally to teleoperation of computer-assisted devices and more particularly to techniques for following commands of an input device using a constrained proxy.

BACKGROUND

Computer-assisted systems are often used to teleoperatively control a device to perform procedures in a workspace (e.g., an interior anatomy of a patient in a medical example). In an example teleoperative system, an operator at an operator station manipulates a leader device (e.g., an input device configured to accept commands for a follower device) that is converted to motions of a follower device (e.g., a manipulator system configured to follow the leader device, a repositionable structure with or without a supported instrument) in the workspace. In an example, to improve the usability of the system, motions of the leader device relative to an operator frame of reference (e.g. of an part of the operator's anatomy, such as the operator's eyes, head, or torso; of a part of a display unit configured to display images of the workspace to the operator, etc.) are used to determine corresponding motion commands for the follower device relative to an imaging device that captures the images that are displayed on the display device.

The ability of a teleoperated device to perform the commanded motions (e.g., for a teleoperated follower-type device to follow the commands derived from motions of a leader device) is subject to practical constraints. In some examples, the teleoperated device may be subject to motion limits, such as range of motion limits, kinematic limits, acceleration limits, velocity limits, current limits, voltage limits, power limits, loading limits, etc. of components such as actuators, links, and joints. In some examples, the teleoperated device may be constrained based on the physical design, the materials selection, the components used, and/or a current position, physical configuration, and/or orientation of the follower device. For example, when the follower device is in certain poses (where a pose refers to a position, an orientation, or a position and orientation) and/or physical configuration, the follower device may be able to accurately and quickly follow the commanded motions of the leader device. However, when the follower device is in certain other poses and/or physical configurations where motion of the follower device is more restricted or hindered, the ability of follower device to follow the commanded motions of the leader device may decrease significantly.

Under certain conditions, these practical constraints on the follower device may limit the ability of the follower device to follow the commands of the leader device as accurately or as quickly as desired. For example, the motion of the follower device in response to a commanded motion may occur with a slower speed or deviation that is detectable by unaided human senses, or annoying to human operators. As leader-follower examples, a follower device may have limited ability to make the same amount of motion as a leader device, to move as quickly as the leader device, or to move as accurately as desired given the movement of the leader device.

Accordingly, improved techniques for a follower device of a teleoperative system to follow commands of leader device are desirable. Techniques for following commands of an input device using a constrained proxy include a computer-assisted device having an input control, a functional structure, and a processing system. The functional structure is configured to include a repositionable structure, and the repositionable structure is configured to support an instrument. The processing system is configured to receive a movement command from the input control, update a pose of a proxy based on the movement command and a proxy constraint, and cause the functional structure to move based on the updated pose of the proxy. The proxy constraint limits possible poses of the proxy.

SUMMARY

Consistent with some embodiments, a computer-assisted device includes an input control, a functional structure, and a processing system. The functional structure is configured to include a repositionable structure, and the repositionable structure is configured to support an instrument. The processing system is configured to receive a movement command from the input control, update a pose of a proxy based on the movement command and a proxy constraint, and cause the functional structure to move based on the updated pose of the proxy.

The proxy constraint limits possible poses of the proxy.

Consistent with some embodiments, a method performed by a processing system includes receiving a movement command from an input control of a computer-assisted device, updating a pose of a proxy based on the movement command and a proxy constraint, and causing a functional structure of the computer-assisted device to move based on the updated pose of the proxy. The proxy constraint limits possible poses of the proxy.

Consistent with some embodiments, one or more non-transitory machine-readable media include a plurality of machine-readable instructions which when executed by one or more processors are adapted to cause the one or more processors to perform any of the methods described herein.

BRIEF DESCRIPTION OF THE DRAWINGS

FIGS. 3A-3E illustrate motion of a follower device in response to a commanded motion of a leader device in accordance with one or more embodiments.

FIG. 4 is a flow diagram of method steps for a follower device of a teleoperative system to follow commands of a leader device in accordance with one or more embodiments.

FIGS. 6A-6E illustrate motion of a follower device, in the frame of reference of the follower device, in response to a commanded motion of a leader device in accordance with one or more embodiments.

Figure 1:
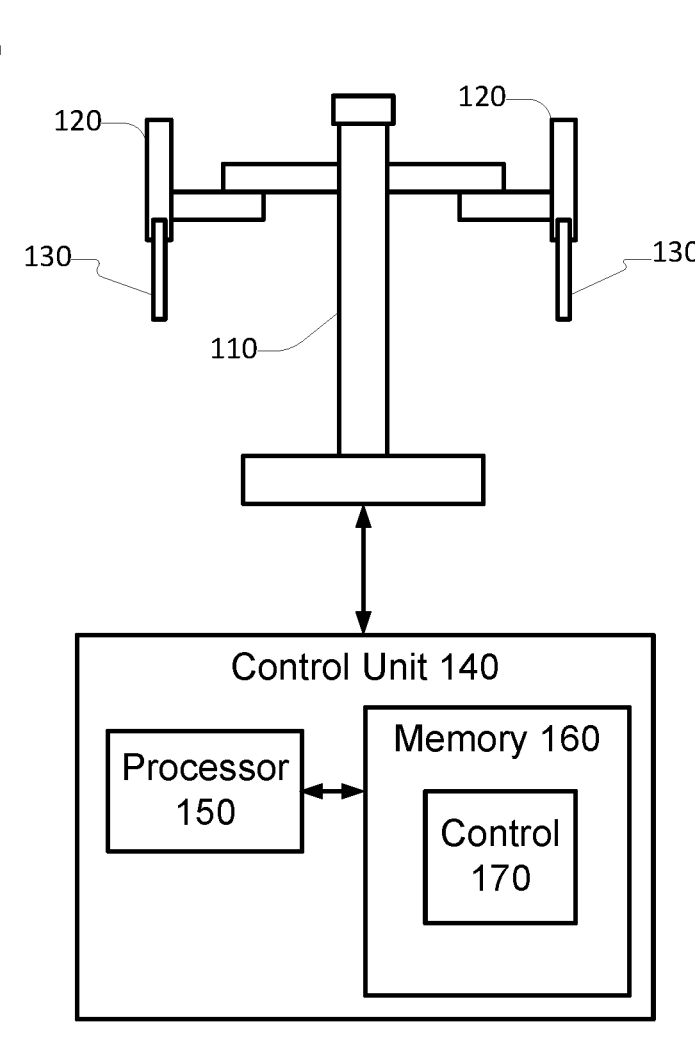
FIG. 1 is a diagram of a first teleoperative system in accordance with one or more embodiments.

In the figures, elements having the same designations have the same or similar functions.

DETAILED DESCRIPTION

In this description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

Further, the terminology in this description is not intended to limit the invention. For example, spatially relative terms-such as "beneath", "below", "lower", "above", "upper", "proximal", "distal", and the like-may be used to describe the relation of one element or feature to another element or feature as illustrated in the figures. These spatially relative terms are intended to encompass different positions (i.e., locations) and orientations (i.e., rotational placements) of the elements or their operation in addition to the position and orientation shown in the figures. For example, if the content of one of the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly. Likewise, descriptions of movement along and around various axes include various special element positions and orientations. In addition, the singular forms "a", "an", and "the" are intended to include the plural forms as well, unless the context indicates otherwise. And, the terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

Elements described in detail with reference to one embodiment, implementation, or module may, whenever practical, be included in other embodiments, implementations, or modules in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions.

In some instances, well known methods, procedures, components, and circuits have not been described in detail so as not to unnecessarily obscure aspects of the embodiments.

This disclosure describes various devices, elements, and portions of computer-assisted devices and elements in terms of their state in three-dimensional space. As used herein, the term "position" refers to the location of an element or a portion of an element in a three-dimensional space (e.g., three degrees of translational freedom along Cartesian x-, y-, and z-coordinates). As used herein, the term "orientation" refers to the rotational placement of an element or a portion of an element (three degrees of rotational freedom—e.g., roll, pitch, and yaw, angle-axis, rotation matrix, quaternion representation, and/or the like). As used herein, the term "shape" refers to a set positions or orientations measured along an element. As used herein, and for a device with repositionable arms and/or other repositionable structures, the term "proximal" refers to a direction toward the base of the computer-assisted device along the kinematic chain of the computer-assisted device and "distal" refers to a direction away from the base along the kinematic chain.

As used herein, the term "pose" refers to the multi-degree of freedom (DOF) spatial position and orientation of a coordinate system of interest attached to a rigid body. In general, a pose includes a pose variable for each of the DOFs in the pose. For example, a full 6-DOF pose would include 6 pose variables corresponding to the 3 positional DOFs (e.g., x, y, and z) and the 3 orientational DOFs (e.g., roll, pitch, and yaw). A 3-DOF position only pose would include only pose variables for the 3 positional DOFs. Similarly, a 3-DOF orientation only pose would include only pose variables for the 3 rotational DOFs. Further, a velocity of the pose captures the change in pose over time (e.g., a first derivative of the pose). For a full 6-DOF pose, the velocity would include 3 translational velocities and 3 rotational velocities. Poses with other numbers of DOFs would have a corresponding number of velocities translational and/or rotational velocities.

Aspects of this disclosure are described in reference to computer-assisted systems and devices, which may include systems and devices that are teleoperated, remote-controlled, autonomous, semiautonomous, robotic, and/or the like. Further, aspects of this disclosure are described in terms of an implementation using a surgical system, such as the da Vinci® Surgical System commercialized by Intuitive Surgical, Inc. of Sunnyvale, California. Knowledgeable persons will understand, however, that inventive aspects disclosed herein may be embodied and implemented in various ways, including robotic and, if applicable, non-robotic embodiments and implementations. Implementations on da Vinci® Surgical Systems are merely exemplary and are not to be considered as limiting the scope of the inventive aspects disclosed herein. For example, techniques described with reference to surgical instruments and surgical methods may be used in other contexts. Thus, the instruments, systems, and methods described herein may be used for humans, animals, portions of human or animal anatomy, industrial systems, general robotic, or teleoperational systems. As further examples, the instruments, systems, and methods described herein may be used for non-medical purposes including industrial uses, general robotic uses, sensing or manipulating non-tissue work pieces, cosmetic improvements, imaging of human or animal anatomy, gathering data from human or animal anatomy, setting up or taking down systems, training medical or non-medical personnel, and/or the like. Additional example applications include use for procedures on tissue removed from human or animal anatomies (without return to a human or animal anatomy) and for procedures on human or animal cadavers. Further, these techniques can also be used for medical treatment or diagnosis procedures that include, or do not include, surgical aspects.

FIG. 1 is a diagram of a first teleoperative system 100 in accordance with one or more embodiments. As shown in FIG. 1, the first teleoperative system 100 includes a computer-assisted device 110 with one or more repositionable arms 120, also referred to herein as repositionable structures. Each of the one or more repositionable arms 120 can support one or more manipulators and/or one or more instruments 130. In some examples, the computer-assisted device 110 can be consistent with a computer-assisted surgical device. The one or more repositionable arms 120 can each provide support for the instruments 130 such as medical instruments, imaging devices, and/or the like. Examples of medical instruments include surgical instruments for interacting with tissue, imaging, sensing devices, and/or the like. In some examples, the instruments 130 can include end effectors that are capable of, but are not limited to, performing, gripping, retracting, cauterizing, ablating, suturing, cutting, stapling, fusing, sealing, etc., and/or combinations thereof. In some examples, the manipulators and/or instruments 130 are removably attached to each other and/or to the repositionable structure. Additionally or alternatively, the manipulators and/or instruments 130 are permanently attached to each other and/or to the repositionable structure, such as an end effector that is permanently attached at the end of a manipulator. As described herein, a functional structure refers to the repositionable structure or, in the alternative, to the repositionable structure along with the one or more manipulators and/or one or more instruments 130 supported by the repositionable structure.

The computer-assisted device 110 can further be coupled to an operator station (not shown), which can include one or more input controls, also referred to herein as input devices, for operating the computer-assisted device 110, the one or more repositionable arms 120, and/or the instruments 130. In some examples, the one or more input controls can include manipulators, levers, pedals, switches, keys, knobs, triggers, and/or the like. In some embodiments, the computer-assisted device 110 and the operator station may correspond to a da Vinci® Surgical System commercialized by Intuitive Surgical, Inc. of Sunnyvale, California. In some embodiments, computer-assisted devices with other configurations, fewer or more repositionable arms, and/or the like may be used with the first teleoperative system 100.

The computer-assisted device 110 is coupled to a control unit 140 via an interface. The interface can be wired and/or wireless, and can include one or more cables, fibers, connectors, and/or buses and can further include one or more networks with one or more network switching and/or routing devices. Operation of the control unit 140 is controlled by a processor 150. And although the control unit 140 is shown with only one processor 150, it is understood that the processor 150 is representative of one or more central processing units, multi-core processors, microprocessors, microcontrollers, digital signal processors, field programmable gate arrays (FPGAs), application specific integrated circuits (ASICs), graphics processing units (GPUs), tensor processing units (TPUs), and/or the like in the control unit 140. The control unit 140 can be implemented as a standalone subsystem and/or board added to a computing device or as a virtual machine. In some embodiments, the control unit 140 can be included as part of the operator station and/or operated separately from, but in coordination with the operator station.

The memory 160 can be used to store software executed by the control unit 140 and/or one or more data structures used during operation of the control unit 140. The memory 160 can include one or more types of machine-readable media. Some common forms of machine-readable media can include floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip, or cartridge, and/or any other medium from which a processor or computer is adapted to read.

As shown in FIG. 1, the memory 160 includes a control module 170 that can be used to support autonomous, semiautonomous, and/or teleoperated control of the computer-assisted device 110. The control module 170 can include one or more application programming interfaces (APIs) for receiving position, motion, force, torque, and/or other sensor information from the computer-assisted device 110, the repositionable arms 120, and/or the instruments 130, exchanging position, motion, force, torque, and/or collision avoidance information with other control units regarding other devices, and/or planning and/or assisting in the planning of motion for the computer-assisted device 110, the repositionable arms 120, and/or the instruments 130. In some examples, the control module 170 further supports autonomous, semiautonomous, and/or teleoperated control of the instruments 130 during the performance of various tasks. And although the control module 170 is depicted as a software application, the control module 170 can optionally be implemented using hardware, software, and/or a combination of hardware and software.

In a teleoperation scenario, the input controls comprise leader devices (also called "master" devices in industry), and the one or more repositionable arms 120 and/or the instruments 130 comprise follower devices (also called "slave" devices in industry). An operator can use the input controls to command motion of the repositionable arms and/or the instruments 130, in a leader-follower configuration. The leader-follower configuration is also often called a teleoperation configuration or sometimes called a master-slave configuration in industry.

In some medical embodiments, the first teleoperative system 100 may be found in a clinic, diagnostic facility, an operating room, or an interventional suite. Although the first teleoperative system 100 includes only one computer-assisted device 110 with two repositionable arms 120 and corresponding instruments 130, one of ordinary skill would understand that the first teleoperative system 100 may include any number of computer-assisted devices with repositionable arms and/or instruments of similar and/or different in design from the computer-assisted device 110. In some examples, each of the computer-assisted devices may include fewer or more repositionable arms and/or instruments.

The leader-follower configuration can pose challenges. As a specific leader-follower example, in a system with constrained conditions, as the leader device moves and commands the follower device to a new pose at a rate faster than the follower can move, the follower device lags the command. When this occurs in this system, the follower device continues to move toward the command, even though the leader device has stopped moving or is moving in a manner different from the command. This behavior may result in motions of the follower device that differs from what is expected or desired by some operators, and may feel unintuitive, disorienting, unexpected, or annoying.

As a specific example, in an example leader-follower instance, the leader device may move to the left in the reference frame used by the leader device, which commands the follower device to correspondingly move left in the reference frame used by the follower device. Under constrained conditions where the follower cannot achieve the rate commanded by the leader device, the follower device may move to the left at a slower speed than commanded, such that follower device lags behind and becomes offset from the commanded pose. If the leader device then begins to move to the right before the follower device has achieved the follower pose that corresponds to the updated pose of the leader device, then the updated pose of the leader device commands the follower device to an updated pose in the reference frame of the follower device that is still to the left of the current pose of the follower device. In this case, the follower device would continue to move left towards the updated commanded pose, even though the leader device is moving toward the right, resulting in a current movement of the follower device in a direction apparently opposite to the current direction of motion of the leader device. In the previous example, if the leader device instead stops moving before the follower device has reached the commanded pose corresponding to the pose of the leader device, the follower device would continue to move left towards the commanded pose even though the leader device has stopped moving, resulting in a movement of the follower device even when there is no movement of the leader device.

To address the described issues, the leader device controls a pose of a virtual leader device. A proxy is introduced, where the pose of the proxy is based on the movement commanded by the virtual leader device and limited, where applicable, by one or more constraints applied to the proxy based on the pose of a virtual follower device. The virtual follower device then follows the pose of the proxy rather than the pose of the virtual leader device. The control module 170 moves the functional structure based on the pose of the virtual follower device. In many cases, the improved approach provides movement of the functional structure in a more intuitive manner than approaches that do not use the proxy.

Figure 2:
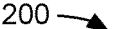
FIG. 2 is a diagram of a second teleoperative system in accordance with one or more embodiments.

FIG. 2 is a diagram of a second teleoperative system 200 in accordance with one or more embodiments. The second teleoperative system 200, in the example of FIG. 2, includes a teleoperative assembly 210 and a user input system 250. In a teleoperation scenario, an operator 298 can use the user input system 250 to operate the teleoperative assembly 210, such as in a leader-follower configuration (also often called a teleoperation configuration or sometimes called a master-slave configuration in industry) of the second teleoperative system 200. In the leader-follower configuration, the user input system 250 is the leader, and the teleoperative assembly 210 is the follower.

The teleoperative assembly 210 can be used to introduce a set of instruments to a work site through a single port 230 (e.g., using a cannula is shown) inserted in an aperture. In a medical scenario, the work site can be on or within a body cavity of a patient, and the aperture can be a minimally invasive incision or a natural body orifice. The port 230 can be held by a linkage 222. The linkage 222 can be coupled to additional joints and links 214, 220 of the teleoperative assembly 210, and these additional joints and links 214, 220 can be mounted on a base 212. The linkage 222 can further include a manipulator-supporting link 224. A set of manipulators 226 can couple to the manipulator-supporting link 224. The repositionable structure that can be moved to follow commands from input controls included in the user input system 250 comprises one or more of any of the following: the linkage 222, additional joints and links 214, 220, base 212, manipulator-supporting link 224, and/or any additional links or joints coupled to the foregoing joints or links. Each of the manipulators 226 can include a carriage (or other instrument-coupling link) configured to couple to an instrument, and each of the manipulators 226 can include one or more joint(s) and/or link(s) that can be driven to move the carriage. For example, a manipulator 226 can include a prismatic joint that, when driven, linearly moves the carriage and any instrument(s) coupled to the carriage. This linear motion can be along an insertion axis that extends through port 230. In some examples, the manipulators 226 and/or instruments are removably attached to each other and/or to the repositionable structure. Additionally or alternatively, the manipulators 226 and/or instruments are permanently attached to each other and/or to the repositionable structure, such as an end effector that is permanently attached at the end of a manipulator 226. As described herein, a functional structure refers to the repositionable structure or, in the alternative, to the repositionable structure along with the one or more manipulators 226 and/or one or more instruments 130 supported by the repositionable structure.

The additional joints and additional links 214, 220 can be used to position the port 230 at the aperture or another location. FIG. 2 shows a prismatic joint for vertical adjustment (as indicated by arrow "A") and a set of rotary joints for horizontal adjustment (as indicated by arrows "B" and "C"). The linkage 222 is used to teleoperatively pivot the port 230 (and the instruments disposed within the port at the time) in yaw, pitch, and roll angular rotations about a remote center of motion located in proximity to port 230 as indicated by arrows D, E, and F, respectively. Such pivoting motions are configured to cause no motion of the remote center. In a robotic surgery example, the remote center can be located at the body wall when the teleoperative assembly 210 is performing robotic surgery. The stationarity of the remote center can be due to physical structure (e.g., by the teleoperative assembly 210 physically configured such that motion of the joints do not move the remote center, sometimes referred to as hardware center (HWC)). The stationarity of the remote center can be due to motion control (e.g., by joints of the teleoperative assembly 210 being commanded such that the contemporaneous motion of the joints do not move the remote center, even though joint motion can move the remote center, sometimes referred to as software center (SWC)). The stationarity of the remote center can also be by a combination of physical structure and motion control (e.g., one or more joints are physically configured such that joint motion does not move the remote center, and one or more joints physically capable of moving the remote center are commanded such that contemporaneous joint motion does not move the remote center.)

Actuation of the degrees of freedom provided by joint(s) of the instrument(s) can be provided by actuators disposed in, or whose motive force (e.g., linear force or rotary torque) is transmitted to, the instrument(s). Examples of actuators include rotary motors, linear motors, solenoids, and/or the like. The actuators can drive transmission elements in the teleoperative assembly 210 and/or in the instruments to control the degrees of freedom of the instrument(s). For example, the actuators can drive rotary discs of the manipulator that couple with drive elements (e.g. rotary discs, linear slides) of the instrument(s), where driving the driving elements of the instruments drives transmission elements in the instrument that couple to move the joint(s) of the instrument, or to actuate some other function of the instrument. Accordingly, the degrees of freedom of the instrument(s) can be controlled by actuators that drive the instrument(s) in accordance with control signals. The control signals can be determined to cause instrument motion or other actuation as determined automatically by the system, as indicated to be commanded by movement or other manipulation of the input control devices, or any other control signal. Furthermore, appropriately positioned sensors, e.g., encoders, potentiometers, and/or the like, can be provided to enable measurement of indications of the joint positions, or other data that can be used to derive joint position, such as joint velocity. The actuators and sensors can be disposed in, or transmit to or receive signals from, the manipulator(s) 226.

While a particular configuration of the teleoperative assembly 210 is shown in FIG. 2, those skilled in the art will appreciate that embodiments of the disclosure can be used with any design of teleoperative assembly. For example, a teleoperative assembly can have any number and any types of degrees of freedom, can be configured to couple to a port, can optionally use a port other than a cannula, such as cannula shown in FIG. 2, and/or the like.

In the example shown in FIG. 2, the user input system 250 includes one or more input devices 252 operated by the operator 298. In the example shown in FIG. 2, the one or more input devices 252 are contacted and manipulated by the hands of the operator 298, with one input device for each hand. Examples of such hand-input-devices include any type of device manually operable by human user, e.g., joysticks, trackballs, button clusters, and/or other types of haptic devices typically equipped with multiple degrees of freedom. Position, force, and/or tactile feedback devices (not shown) can be employed to transmit position, force, and/or tactile sensations from the instruments back to the hands of the operator 298 through the input devices 252.

The input devices 252 are supported by the user input system 250 and are shown as mechanically grounded, and in other implementations can be mechanically ungrounded. An ergonomic support 256 can be provided in some implementations; for example, FIG. 2 shows an ergonomic support 256 including forearm rests on which the operator 298 can rest his or her forearms while manipulating the input devices 252. In some examples, the operator 298 can perform tasks at a work site near the teleoperative assembly 210 during a procedure by controlling the teleoperative assembly 210 using the input devices 252.

A display unit 254 is included in the user input system 250. The display unit 254 can display images for viewing by the operator 298. The display unit 254 can provide the operator 298 with a view of the worksite with which the teleoperative assembly 210 interacts. The view can include stereoscopic images or three-dimensional images to provide a depth perception of the worksite and the instrument(s) of the teleoperative assembly 210 in the worksite. The display unit 254 can be moved in various degrees of freedom to accommodate the viewing position of the operator 298 and/or to provide control functions. Where a display unit (such as the display unit 254 is also used to provide control functions, such as to command the teleoperative assembly 210, the display unit also includes an input device (e.g., another input device 252).

When using the user input system 250, the operator 298 can sit in a chair or other support in front of the user input system 250, position his or her eyes to see images displayed by the display unit 254, grasp and manipulate the input devices 252, and rest his or her forearms on the ergonomic support 256 as desired. In some implementations, the operator 298 can stand at the station or assume other poses, and the display unit 254 and input devices 252 can differ in construction, be adjusted in position (height, depth, etc.), and/or the like.

Figures 3A, 3B, 3C, 3D, 3E:
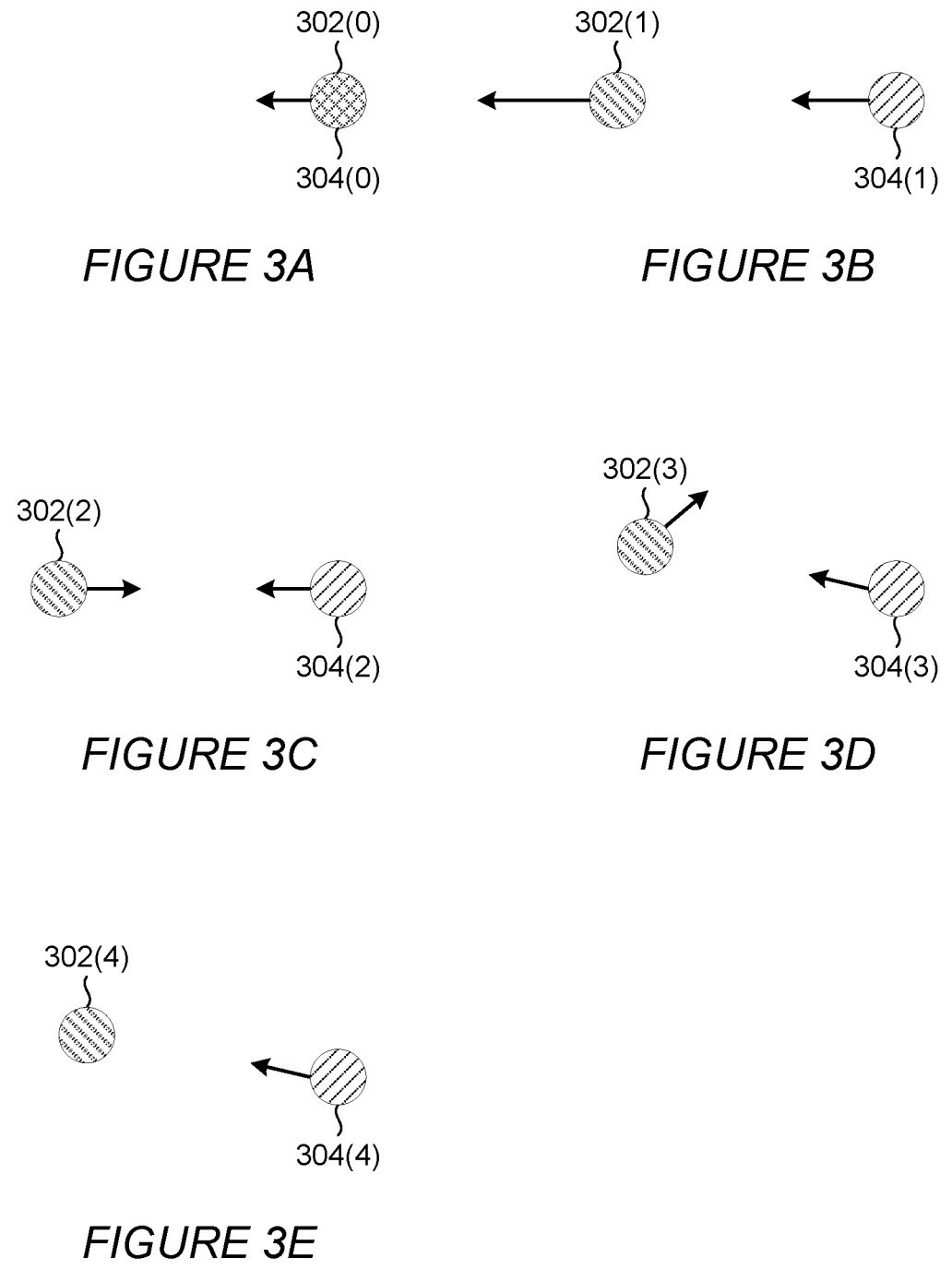

FIGS. 3A-3E illustrate motion of a follower device in response to a commanded motion of a leader device in accordance with one or more embodiments. The motions are shown in FIGS. 3A-3E as rigid body motion in a plane for clarity of explanation. In application, the motions can be more complex, along a one-dimensional line, in a three-dimensional space, etc. As shown in FIG. 3A, the pose of a follower device 304(0) in the reference frame of the follower device 304(0) is coincident with the pose of a leader device 302(0) in the reference frame of the leader device 302(0), where the leader device 302(0) functions as a leader device. When an operator, such as the operator 298 shown in FIG. 2, moves the leader device 302(0) in the reference frame of the leader device 302(0), the follower device 304(0) moves in the reference frame of the follower device 304(0) in response such that the pose of the follower device 304(0) remains coincident with the pose of the leader device 302(0). For example, if the operator 298 moves the leader device 302(0) to the left in the reference frame of the leader device 302(0), as shown in FIG. 3A, the follower device 304(0) also moves left in the reference frame of the follower device 304(0) in response. As a result, the pose of the follower device 304(0) and the pose of the leader device 302(0) remain coincident with one another.

As shown in FIG. 3B, the operator 298 moves the leader device 302(1) to the left in the reference frame of the leader device 302(1), and the follower device 304(1) moves to the left in the reference frame of the follower device 304(1) in response. In this case, although the follower device 304(1) moves in the same direction as the leader device 302(1), the movement of the follower device 304(1) lags behind the movement of the leader device 302(1). As a result, the pose of the follower device 304(1) is not coincident with the pose of the leader device 302(1). This phenomenon can result from one or more source causes.

In some examples, the follower device 304(1) may be subject to certain motion limits. The follower device 304(1) may be subject to position and/or orientation (e.g., pose) limits that do not allow the follower device 304(1) to be at certain positions and/or orientations in physical space. Additionally or alternatively, the follower device 304(1) may be subject to range of motion limits that do not allow the follower device 304(1) to be more than a maximum allowable distance from a reference point. The limits may be based on a hardware limitation, such as the physical configuration or limits of the various components of the first teleoperative system 100 of FIG. 1 or the second teleoperative system 200 of FIG. 2. Additionally or alternatively, the limits may be based on a software limitation, imposed by an application program executing on a processor, such as the processor 150 of the first teleoperative system 100 of FIG. 1. The software limits may, for example, impose motion limits on the follower device 304(1) in order to cause a remote center of motion to remain at a particular position, to avoid damage to the teleoperative system, to avoid damage to an object being manipulated by the teleoperative system, to prevent the follower device from entering certain regions, and/or the like.

In some examples, the follower device 304(1) may be subject to certain velocity and/or acceleration limits. Certain portions of the follower device 304(1), such as actuators, joints, and/or the like, may be subject to a maximum velocity and/or a maximum acceleration. Again, the limits may be based on a hardware limitation, such as the physical configuration or limits of the various components of the first teleoperative system 100 of FIG. 1 or the second teleoperative system 200 of FIG. 2. Additionally or alternatively, the limits may be based on a software limitation, imposed by an application program executing on a processor, such as the processor 150 of the first teleoperative system 100 of FIG. 1. The software limits may, for example, impose velocity and/or acceleration limits on the follower device 304(1) in order to cause a remote center of motion to remain at a particular position, to avoid damage to the teleoperative system, to avoid damage to an object being manipulated by the teleoperative system, to prevent the follower device from entering certain regions, and/or the like.

In some examples, the follower device 304(1) and/or an associated repositionable structure may be subject to certain singularities that may limit the amount and/or direction of movement of the follower device 304(1).

In an example hardware architecture, in order to minimize motion at a remote center of motion, the multiple axes of movement of the functional structure intersect at the remote center of motion. As the functional structure moves to control the follower device 304(1) to follow the commanded motions of the leader device 302(1), a first axis provided by a first joint can become colinear with a second axis provided by a second joint. These two axes provide two distinct degrees of freedom when not colinear. Colinearity of these two axes reduces the two degrees of freedom to one degree of freedom. As the two axes approach colinearity, the ability of the follower device 304(1) to be moved about distinct DOFs using those two joints is reduced.

In addition, if the follower device 304(1) is positioned close to the remote center of motion, any movement of the functional structure around one or more axes intersecting the remote center of motion results in reduced ability to move the follower device 304(1) around the certain axes, limiting the ability to move the follower device 304(1) in a direction orthogonal to the insertion axis. Note that these singularities and/or different additional singularities can be possible with different device configurations. In some examples, the calculations using the kinematic models and/or the Jacobian for each of the functional structures and/or the follower devices 304(1) can be used to generate various numerical parameters, including (a) the distance to a singularity and/or (b) the shape of the proxy constraint, as described herein.

When the follower device 304(2) is subject to one or more limits, as described herein, further movement of the follower device 304(2) can be different than what is expected or desired by the operator 298, and may be unintuitive, disorienting, unexpected, or annoying. As shown in FIG. 3C, the operator 298 has moved the leader device 302(2) to the right in the reference frame of the leader device 302(2) before the follower device 304(2) has moved in the reference frame of the follower device 304(2) to be coincident with the leader device 302(2). As a result, the pose of the leader device 302(2) is still to the left of the pose of the follower device 304(2). Therefore, the follower device 304(2) continues to move to the left in the reference frame of the follower device 304(2), towards the pose of the leader device 302(2) even though the operator 298 is moving the leader device 302(2) to the right. The operator 298 can find such movement undesirable because the follower device 304(2) moves to the left, apparently in response to the operator 298 moving the leader device 302(2) to the right.

As shown in FIG. 3D, the operator 298 has moved the leader device 302(3) upwards and to the right in the reference frame of the leader device 302(3) before the follower device 304(3) has moved in the reference frame of the follower device 304(3) to be coincident with the leader device 302(3). As a result, the pose of the leader device 302(3) is upwards and to the left of the pose of the follower device 304(3). Therefore, the follower device 304(3) moves upwards and to the left in the reference frame of the follower device 304(3), towards the pose of the leader device 302(3). The operator 298 may find such movement undesirable because the follower device 304(3) moves upwards and to the left, apparently in response to the operator 298 moving the leader device 302(3) upwards and to the right.

In response to such nonintuitive movement, the operator 298 may stop moving the leader device 302(4) with the intent of stopping movement of the follower device 304(4). As shown in FIG. 3E, the operator 298 has stopped moving the leader device 302(4) before the follower device 304(4) has moved in the reference frame of the follower device 304(4) to be coincident with the leader device 302(4). As shown, the pose of the leader device 302(4) in the reference frame of the of the leader device 302(4) is upwards and to the left of the pose of the follower device 304(4) in the reference frame of the follower device 304(4). Therefore, the follower device 304(4) continues to move upwards and to the left in the reference frame of the follower device 304(4), towards the pose of the leader device 302(4) in the reference frame of the leader device 302(4), even though the leader device 302(4) is not moving. Again, the operator 298 may find such movement uncontrolled because the follower device 304(4) moves upwards and to the left, apparently without any movement of the leader device 302(4). Note that, although the examples presented in FIGS. 3A-3E are described using poses having two positional DOFs, the same issues described in the context of FIGS. 3A-3E may be present for poses having one DOF or three or more DOFs. Further, the same issues described in the context of FIGS. 3A-3E may be present for poses having positional and/or orientation DOFs in any quantity and in any combination.

To address the described issues, an improved approach involves introducing a proxy between the leader device 302 and the follower device 304. The leader device controls movement of a virtual leader device. The pose of the proxy is based on the movement of the virtual leader device and limited, where applicable, by one or more constraints applied to the proxy based on the pose of a virtual follower device. The proxy is constrained based on the pose of the virtual follower device, such that the pose of the proxy is limited in at least one degree of freedom based on the pose of the virtual follower device. The virtual follower device then follows the pose of the proxy rather than the pose of the virtual leader device. The control module 170 moves the functional structure based on the pose of the virtual leader device. In many cases, the improved approach provides movement of the follower device 304 in a more intuitive manner than approaches that do not use the proxy.

With the disclosed approach, a processor in a teleoperation system detects motion of a leader device (that is, an input device). In some examples, the disclosed approach may be implemented in any teleoperative system, such as the first teleoperative system 100 shown in FIG. 1 or the second teleoperative system 200 shown in FIG. 2. Further, the techniques may be implemented via any technically feasible processor, such as the processor 150 executing the control module 170 shown in FIG. 1. The processor maps the motion of the leader device in physical space to a motion of a virtual leader device in virtual space. The processor moves a proxy in virtual space based on motion of the virtual leader device. The proxy is constrained to be within a proxy constraint defined based on virtual follower device in virtual space (e.g., such as a maximum allowable distance between the proxy and a corresponding pose of the virtual follower device). The processor causes the virtual follower device to move based on the proxy motion/position/orientation. The processor updates the proxy constraint based on an updated pose of the virtual follower device.

The disclosed approach can include blending both position-based approaches and velocity-based approaches, as expressed in Equations 1-5 below:

$$P\_intermediate = P\_proxy[k-1] + (V\_leader[k] * \Delta t) \tag{1}$$

$$P\_proxy[k] = \tag{2}$$

$$P\_follower[k-1] + constrained(P\_intermediate - P\_follower[k-1])$$

$$V\_proxy[k] = (P\_proxy[k] - P\_proxy[k-1]/\Delta t \tag{3}$$

$$V\_follower = \tag{4}$$

$$gamma * V\_proxy[k] + lambda * (P\_proxy[k-1] - P\_follower[k-1])$$

$$P\_follower[k] = P\_follower[k-1] + (V\_follower * \Delta t) \tag{5}$$

In general, a teleoperative system, such as the first teleoperative system 100 shown in FIG. 1 or the second teleoperative system 200 shown in FIG. 2, performs various procedures as a series of machine steps. At each machine step, the teleoperative system performs one or more of receiving a movement command from the leader device, mapping the movement command to a movement of the virtual leader device, updating a pose of a proxy based on the movement of the virtual leader device and a proxy constraint, causing a virtual follower device to move in accordance with the updated pose of the proxy, and causing a functional structure to move in accordance with the motion of the virtual follower device. As described herein, the virtual follower device is a virtual version of the functional structure. As a result, poses and/or motion of the virtual follower device are equivalent to poses and/or motion of the functional structure. The term "k" in Equations 1-5 represents the current machine step, "k−1" represents the previous machine step, and "Δt" represents the time difference between machine step "k" and machine step "k−1." In Equation 1, an intermediate pose of the proxy is determined based on the previous pose of the proxy (P_proxy[k−1]) if the proxy is moved at the velocity of the virtual leader device (V_leader[k]) over the machine step time difference of Δt. The P_intermediate term represents the proxy pose (P_proxy[k]) if the proxy is not subject to proxy constraints. In Equation 2, the updated pose of the proxy is constrained based on the constraint term to limit where the proxy can move relative to the virtual follower device. Equation 3 yields the velocity of the proxy (V_proxy[k]) based on the current position of the proxy (P_proxy[k]) and the prior position of the proxy (P_proxy[k−1]). The velocity of the proxy (V_proxy[k]) is a modified version of the velocity of the virtual leader device (V_leader[k]). In Equations 4 and 5, the velocity of the virtual follower device (V_follower) is determined based on: (a) the velocity of the proxy (the gamma term of equation 4); (b) the virtual follower device pose to proxy pose correction (the lambda term of equation 4); or (c) a combination of both (a) and (b), based on the coefficients gamma and lambda. If gamma=0 and lambda is non-zero, then the virtual follower device velocity is based solely on the position correction. If gamma=1 and lambda=0], then the virtual follower device becomes coincident with the proxy. In some embodiments, reasonable ranges for the parameters are gamma=[0, 1] and lambda=[0, 1/Δt]. In some embodiments, the parameters can be set to values which are not at maximum values, e.g., gamma=0, lambda=0.1/Δt and/or are configurable based on one or more of a type of the functional structure, a procedure being performed, operator preference, and/or the like. This describes an Euler integration approach. In some embodiments, other numerical integration approaches can be used.

In some embodiments, the inverse kinematics of the virtual follower device is considered. In such embodiments, the pose of the virtual follower device computed in Equation 5 changes, as shown in Equation 5B below:

$$P\_follower[k] = f(P\_follower[k-1], V\_follower, \Delta t) \tag{5B}$$

Equation 5B applies function f(*) to account for the inverse kinematics of the virtual follower device without perfect inverse kinematics. Without perfect inverse kinematics, some error build-up can result over time, motivating, at least in part, the need for a correction term. If inverse kinematics of the proxy is also considered, then Equations 1 and 2 also change, as shown in Equations 1B and 2B below:

$$P\_intermediate = h(P\_proxy[k-1], (V\_leader[k], \Delta t) \tag{1B}$$

$$P\_proxy[k] = \tag{2B}$$

$$g(P\_follower[k-1], constrained(P\_intermediate - P\_follower[k-1]))$$

The f(*) function of Equation 5B and the h(*) function of Equation 1B represent how the joint kinematics are taken into account while combining pose and velocity terms as input in order to determine a pose output. The g(*) function of Equation 2B represents how the joint kinematics are taken into account while combining only pose terms as input in order to determine a pose output. Further, the f(*) function involves the joint kinematics of the virtual follower device, while the g(*) and h(*) functions involve the joint kinematics of the proxy. For example, the f(*), g(*), and h(*) functions account for the joint kinematics by applying a corresponding inverse kinematic model to map an input pose within the workspace or reach of the kinematic structure (e.g., proxy or virtual follower device) to changes in the joint kinematic variables of the kinematic structure and then mapping the changes in the joint kinematic variables to an output pose in the reference frame of the kinematic structure using a forward kinematic model. The rationale for this approach is that the reference frame is not altered whether or not using the joint kinematics. However, the virtual leader device can be directing the proxy or virtual follower device to move to a pose where the proxy and/or the virtual follower device cannot go, in which case joint kinematics would reveal this issue. In such cases, the h(*) function of Equation 1B, the g(*) function of Equation 2B, and/or the f(*) function of Equation 5B are employed to determine a target pose and/or target velocity for the proxy and/or the virtual follower device.

FIG. 4 is a flow diagram of method steps for a follower device of a teleoperative system to follow commands of a leader device in accordance with one or more embodiments. Although the method steps are described in conjunction with the systems of FIGS. 1-3E and 5A-6E, persons of ordinary skill in the art will understand that any system configured to perform the method steps, in any order, is within the scope of the present disclosure. One or more of the processes 402-412 of method 400 may be implemented, at least in part, in the form of executable code stored on non-transient, tangible, machine-readable media. This executable code, when executed by one or more processors (e.g., the processor 150 in the control unit 140), can cause the one or more processors to perform one or more of the processes 402-412. In some embodiments, method 400 can be performed by a module, such as the control module 170. In some embodiments, method 400 can be used by a follower device of a teleoperative system to follow commands of a leader device via a proxy that is constrained based on the follower device.

Aspects of method 400 are described via reference to FIGS. 5A-5L, which illustrate various proxy constraints that limit possible poses of a proxy in accordance with one or more embodiments, and FIGS. 6A-6E illustrate motion of a follower device, in the frame of reference of the follower device, in response to a commanded motion of a leader device in accordance with one or more embodiments. However, it is understood that the examples of FIGS. 5A-5L and FIGS. 6A-6E are non-limiting and that other values, shapes, behaviors, and/or the like depicted in FIGS. 5A-5L and FIGS. 6A-6E may be different for different leader devices, different follower devices, different functional structures, different DOFs, different tasks, and/or the like.

At a process 402, a processor, such as the processor 150 in the control unit 140, receives a movement command from an input device. More specifically, the processor receives a movement command from an input device (e.g., a leader device), such as by detecting motion of one or more of the input devices shown in FIGS. 1-3E in response to being manipulated by the operator 298. For example, the input devices can be contacted and manipulated by the hands of the operator 298, such as with one input device for each hand. Examples of such hand-input-devices include any type of device manually operable by human user, e.g., joysticks, trackballs, button clusters, and/or other types of haptic devices typically equipped with multiple degrees of freedom. The input devices are supported by a user input system and can be mechanically grounded or mechanically ungrounded. The changes in position and/or orientation (e.g., pose) of one or more input devices in the reference frame of the input devices are detected and translated into one or more movement commands.

At a process 404, the processor determines a motion of a virtual leader device based on the movement commands from the input device. The processor maps the motion of the input device in physical space to a motion of a virtual leader device in virtual space. In some embodiments, the change in position and/or orientation (e.g., pose) of the virtual leader device is a function of a current velocity (e.g., V_leader[k]) of the virtual leader device and the change in time between two machine steps ($\Delta t$), as expressed in Equations 1 and 1B. Depending upon the implementation, the pose of the virtual leader device and the current velocity of the virtual leader device can include one or more pose variables corresponding to the positional and/or orientational DOFs of the virtual leader device.

At a process 406, the processor determines a proxy constraint based on a limitation and/or a pose of a virtual follower device, such as one of the virtual follower devices shown in FIGS. 3A-3E. In some embodiments, the proxy constraint is a function of a constraint term (e.g., constrained (P_intermediate–P_follower[k–1]), as expressed in Equations 2 and 2B. Under certain conditions, the ability of a virtual follower device to accurately and quickly follow a motion of a virtual leader device can be reduced due to the current pose of the virtual follower device. Additionally or alternatively, and under certain conditions, the ability of a virtual follower device to follow a commanded motion of the virtual leader device can be reduced due to one or more limitations of the virtual follower device, as described herein. The limitation can be based on a hardware limitation and/or a software limitation. In order to accommodate a reduced ability of the virtual follower device to accurately and quickly follow a commanded motion of the virtual leader device, the processor generates a proxy constraint that limits the motion of the proxy. In some embodiments, the pose of the virtual follower device can correspond to a pose of a predetermined point on or near a portion of the functional structure that corresponds to the virtual follower device (e.g., a distal tip of the functional structure, a pivot point of jaws of the functional structure, a center point of jaws of the functional structure, and/or the like). Additionally or alternatively, in some embodiments, the pose of the virtual follower device can correspond to an orientation of a portion of the functional structure that corresponds to the virtual follower device (e.g., a direction between a pivot point of the jaws of the functional structure and the distal tip of the functional structure). The pose of the virtual follower device may include one or more position pose variables and/or one or more orientation pose variables, in any combination. The proxy constraint can be determined based on one or more of a type of the functional structure, a procedure being performed, operator preference, and/or the like.

The shape and size of the proxy constraint can vary based on the nature of the limitation of the functional structure corresponding to the virtual follower device. In some examples, the proxy constraint can be unbounded in one or more directions. In that regard, some DOFs of the proxy can be constrained while other DOFs of the proxy may be unconstrained. In some examples, the proxy may be constrained in a first direction orthogonal to an insertion direction achieved by motion along a first axis while the proxy may not be constrained in a second direction parallel to the insertion direction achieved by motion along a second axis. In some examples, the size of the proxy constraints can be relatively small. Therefore, although the boundary may not be the same distance in all directions, the shape of the boundary is generally not particularly noticeable to an operator.

The proxy constraint may have a symmetrical boundary shape that exhibits any type of symmetry or may have a boundary shape that lack any type of symmetry. These various symmetrical or asymmetrical boundary shapes can additionally provide isotropic and/or anisotropic constraints, such as based on motion limits, velocity and/or acceleration limits, degree of colinearity between two or more axes of movement, proximity to a remote center of motion, and/or the like. In that regard, the proxy constraints may be different for different DOFs or different combinations of DOFs. More particularly, different combinations of limitations result in different sizes and shapes of proxy constraint volumes for the proxy, where the volume of the proxy constraint around the follower device determines where the proxy may be positioned and/or oriented relative to the pose of the virtual follower device. The proxy constraint may be a one-dimensional (1D), two-dimensional (2D), three-dimensional (3D), and/or any additional number of dimensions based on the number of pose variables and DOFs of the pose of the proxy and/or the pose of the virtual follower device.

Figure 5A:
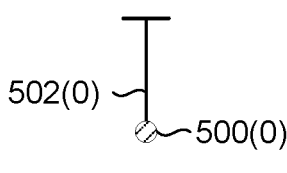
FIGS. 5A-5L illustrate various proxy constraints that limit possible poses of a proxy in accordance with one or more embodiments.
Figure 5B:
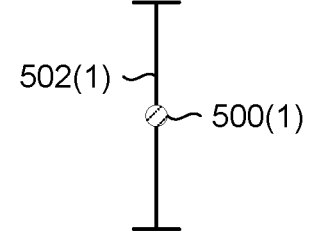

If the virtual follower device is constrained to move along a single DOF, then the proxy constraint may be a one-dimensional line segment. As shown in FIG. 5A, the proxy constraint 502(0) may be a 1D proxy constraint that extends in a single direction from the virtual follower device 500(0). As a result, the proxy is constrained to move along the line segment above the virtual follower device 500(0), as represented by the proxy constraint 502(0). As shown in FIG. 5B, the proxy constraint 502(1) may be a 1D proxy constraint that extends in two directions from the virtual follower device 500(1). As a result, the proxy is constrained to move along the line segment above the virtual follower device 500(1) and/or the line segment below the virtual follower device 500(1), as represented by the proxy constraint 502(1).

Figure 5C:
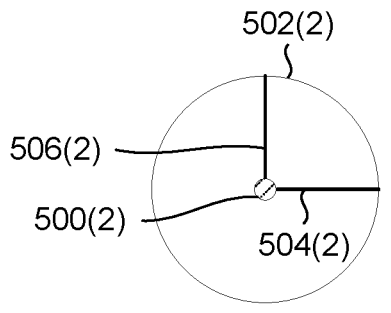
Figure 5D:
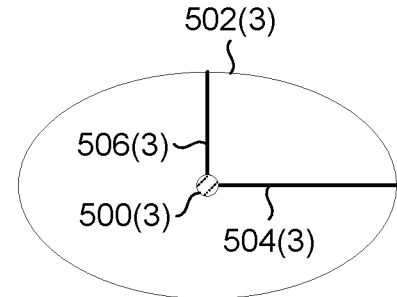

If the virtual follower device is constrained to move along two DOFs, then the proxy constraint may be a two-dimensional area. As shown in FIG. 5C, the proxy constraint 502(2) may be a 2D proxy constraint applied to a combination of two DOFs 504(2) and 506(2) that use distance from the pose of the virtual follower device 500(2) as the constraint. The constraint along a first DOF 504(2) is equal to the constraint along a second DOF 506(2). As a result, the proxy is constrained to move within a circular area surrounding the virtual follower device 500(2), as represented by the proxy constraint 502(2). As shown in FIG. 5D, the proxy constraint 502(3) may be a 2D proxy constraint applied to the combination of a first DOF 504(3) a second DOF 506(3). The constraint constrains the proxy along the first DOF 504(3) more than the proxy is constrained along the second DOF 506(3). As a result, the proxy is constrained to move within an elliptical area surrounding the virtual follower device 500(3), as represented by the proxy constraint 502(3).

Figure 5E:
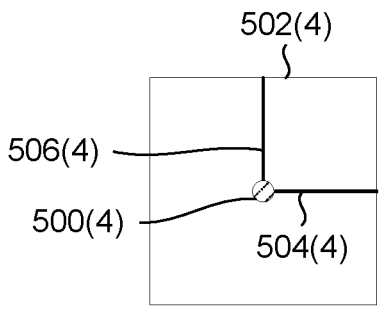
Figure 5F:
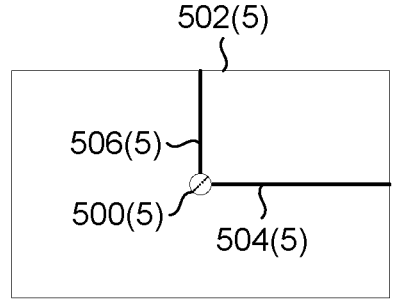

If the virtual follower device is constrained to move along two DOFs, then the proxy constraint may be a two-dimensional area. As shown in FIG. 5E, the proxy constraint 502(4) may be a 2D proxy constraint applied independently to two DOFs 504(4) and 506(4) that use distance from the pose of the virtual follower device 500(4) as the constraint. The constraint along a first DOF 504(4) has the same range as the constraint along a second DOF 506(4). As a result, the proxy is constrained to move within a square area surrounding the virtual follower device 500(4), as represented by the proxy constraint 502(4). As shown in FIG. 5F, the proxy constraint 502(5) may be a 2D proxy constraint applied to a first DOF 504(5) and a second DOF 506(5). The constraint constrains the proxy along the second DOF 506(5) more than the proxy is along the second DOF 506(5). As a result, the proxy is constrained to move within a rectangular area surrounding the virtual follower device 500(5), as represented by the proxy constraint 502(5).

Figure 5G:
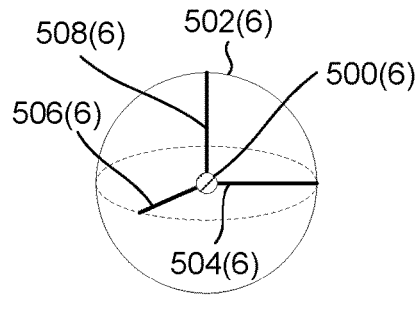
Figure 5H:
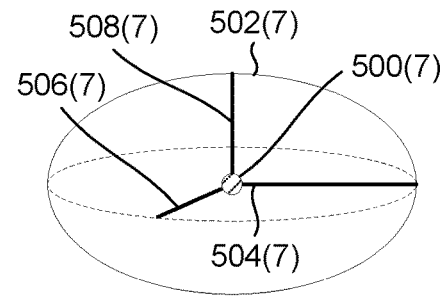

If the virtual follower device is constrained to move along three DOFs, then the proxy constraint may be a three-dimensional enclosed volume. As shown in FIG. 5G, the proxy constraint 502(6) may be a 3D proxy constraint applied to a combination of three DOFs 504(6), 506(6), and 508(6) that use distance from the pose of the virtual follower device 500(6) as the constraint. The constraints are equal along a first DOF 504(6), a second DOF 506(6), and a third DOF 508(6). As a result, the proxy is constrained to move within a spherical volume surrounding the virtual follower device 500(6), as represented by the proxy constraint 502(6). As shown in FIG. 5H, the proxy constraint 502(7) may be a 3D proxy constraint applied to the combination of a first DOF 504(7), a second DOF 506(7), and a third DOF 508(7). The constraint constrains the proxy along the first DOF 504(7) more than the proxy is constrained along either of the second DOF 506(7) or the third DOF 508(7). As a result, the proxy is constrained to move within an ellipsoidal volume surrounding the virtual follower device 500(7), as represented by the proxy constraint 502(7).

If the virtual follower device is constrained to move along three DOFs, then the proxy constraint may be a three-dimensional enclosed volume. The proxy constraint may be a 3D proxy constraint (not shown) applied independently to three DOFs that use distance from the pose of the virtual follower device as the constraint. The constraint has the same range along a first DOF, a second DOF, and a third DOF. As a result, the proxy is constrained to move within a cubical volume surrounding the virtual follower device. The proxy constraint may be a 3D proxy constraint (not shown) applied to the combination of a first DOF, a second DOF, and a third DOF. The constraint constrains the proxy along the first DOF more than the proxy is constrained along either of the second DOF or the third DOF. As a result, the proxy is constrained to move within a rectangular solid volume surrounding the virtual follower device.

Figure 5I:
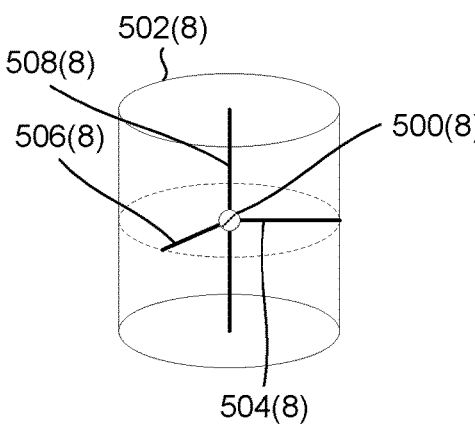
Figure 5J:
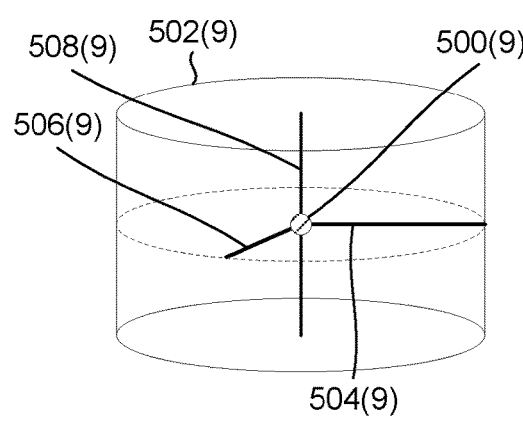

As shown in FIG. 5I, the proxy constraint 502(8) may be a 3D proxy constraint applied to a combination of three DOFs 504(8), 506(8), and 508(8). The proxy constraint 502(8) is applied equally to the combination of the first DOF 504(8) and the second DOF 506(8) based on distance from the virtual follower device 500(8). The proxy constraint 502(8) is applied independently along the third DOF 508(8). As a result, the proxy is constrained to move within a closed circular cylinder surrounding the virtual follower device 500(8), as represented by the proxy constraint 502(8). As shown in FIG. 5J, the proxy constraint 502(9) may be a 3D proxy constraint applied to a combination of three DOFs 504(9), 506(9), and 508(9). The proxy constraint 502(9) is applied to the combination of the first DOF 504(9) and the second DOF 506(9). The proxy constraint 502(8) is applied independently along a third DOF 508(9). As a result, the proxy is constrained to move within a closed elliptical cylinder surrounding the virtual follower device 500(9), as represented by the proxy constraint 502(9).

Figure 5K:
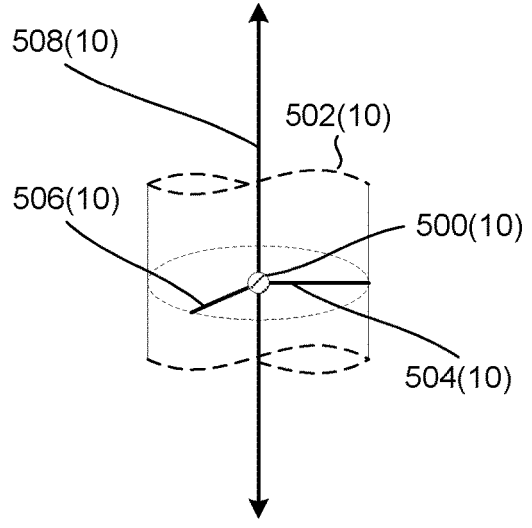
Figure 5L:
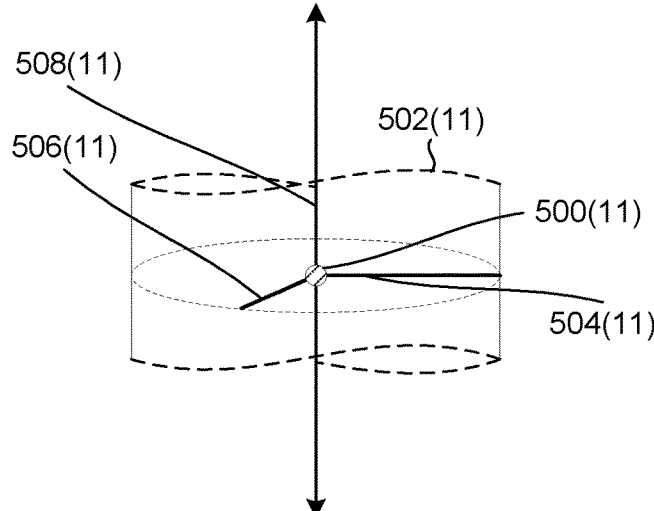

If the proxy is constrained to move along two DOFs and unconstrained in a third DOF, then the proxy constraint may be a three-dimensional open cylindrical volume. As shown in FIG. 5K, the proxy constraint 502(10) may be a 3D proxy constraint applied to a combination of three DOFs 504(10), 506(10), and 508(10). The proxy constraint 502(10) is applied equally to the combination of the first DOF 504(10) and the second DOF 506(10) based on distance from the virtual follower device 500(10). The proxy constraint 502(10) is applied independently along a third DOF 508(10) and is unconstrained. As a result, the proxy is constrained to move within an open circular cylinder surrounding the virtual follower device 500(10), as represented by the proxy constraint 502(10). As shown in FIG. 5L, the proxy constraint 502(11) may be a 3D proxy constraint applied to a combination of three DOFs 504(11), 506(11), and 508(11). The proxy constraint 502(11) is applied to the combination of the first DOF 504(11) and the second DOF 506(11). The proxy constraint 502(11) is applied independently along a third DOF 508(11) and is unconstrained. As a result, the proxy is constrained to move within an open elliptical cylinder surrounding the virtual follower device 500(11), as represented by the proxy constraint 502(11).

In addition to the proxy constraints shown in FIGS. 5A-5L, the proxy constraint may be of any technically feasible shape and/or size. In some examples, even though the proxy constraints shown in FIGS. 5A-5L are shown as constraints on the pose variables of positional DOFs, similar constraints can be applied to pose variables of rotational DOFs and/or positional DOFs, in any combination. In some examples, the proxy constraints may include any combination of constraints on combinations of two or more DOFs and/or independent constraints on one or more additional DOFs to form constraints of up to as many dimensions as pose variables in the pose of the proxy.

The proxy constraint functions to constrain the motion of the proxy and, in turn, to impose a limit on the movement of the virtual follower device in response to movement of the input device. Typically, the boundary of the proxy constraint can be centered at a reference defined based on virtual follower device. Where the virtual follower device corresponds to the functional structure, the proxy constraint can be defined such that it varies based on the pose of the functional structure. Additionally or alternatively, the proxy constraint can be defined such that it varies based on the physical configuration of the functional structure, the velocity of the functional structure, the velocity of the input device, and/or the like. In some examples, the proxy constraint can be more constraining, that is, the size of the proxy constraint may be reduced along one or more DOFs, when the virtual follower device approaches certain regions or configurations with more limited virtual follower device movement. Correspondingly, the proxy constraint can be less constraining, that is, the size of the proxy constraint may be increased along one or more DOFs, when the virtual follower device moves away from such certain regions or configurations with more limited virtual follower device movement. The parameters that define the proxy constraint may vary as the proxy constraint becomes more constraining or less constraining over time. For example, the radius of the circular proxy constraint 502(2) of FIG. 5C may decrease as the proxy constraint 502(2) becomes more constraining or increase as the proxy constraint 502(2) becomes less constraining. Similarly, the length of the major axis and/or the length of the minor axis of the elliptical proxy constraint 502(3) of FIG. 5D may decrease as the proxy constraint 502(3) becomes more constraining or increase as the proxy constraint 502(3) becomes less constraining. The radius and/or the height of the cylindrical proxy constraint 502(8) of FIG. 5I may decrease as the proxy constraint 502(8) becomes more constraining or increase as the proxy constraint 502(8) becomes less constraining, and so on.

In some examples, the extents of a proxy constraint can be narrower near a singularity or other limitation. As a result, the extents of the proxy constraint can vary with proximity to the singularity in those examples, resulting in more constraint on the proxy as the virtual follower device approaches the singularity and less constraint on the proxy as the virtual follower device moves away from the singularity. In some examples, as a first axis of the virtual follower device approaches colinearity with a second axis, the processor generates a proxy constraint applied to a degree of freedom of the proxy movement due to rotations about the first axis. The application of the proxy constraint or the amount to which the proxy constraint limits the motion of the proxy depends on the angle between the first axis and the second axis. In some examples, as a portion of the virtual follower device approaches a remote center of motion, the processor generates a proxy constraint applied to a degree of freedom of the proxy movement. The application of the proxy constraint or the amount to which the proxy constraint limits the motion of the proxy depends on the distance between the portion of the virtual follower device and the remote center of motion.

After determining a proxy constraint, the processor can subsequently determine that the position and/or orientation (e.g., pose) of the virtual follower device is no longer within a threshold of a singularity or other limitation. Under such conditions, the processor can increase the size of the proxy constraint, thereby allowing more freedom of movement for the proxy and, by extension, the virtual follower device. In some examples, the processor can remove the proxy and/or the proxy constraint. In such cases, the virtual follower device follows the input device rather than the proxy.

Returning to FIG. 4, at a process 408, the processor determines the pose of the proxy based on the motion of the virtual leader device and/or the proxy constraint. The processor moves a proxy based on motion of the virtual leader device, such that the proxy is constrained to be within a proxy constraint defined based on the virtual follower device (e.g., such as a maximum allowable distance between the proxy and a corresponding pose of the virtual follower device). In some embodiments, the pose of the proxy is a function of a previous pose of the proxy, the motion of the virtual leader device, the previous pose of the virtual follower device, and a proxy constraint term, as expressed in Equations 1-2 and 1B-2B.

FIGS. 6A-6E illustrate motion of a virtual follower device, in the frame of reference of the virtual follower device, in response to a commanded motion of a leader device, in the frame of reference of the leader device. In general, the frame of reference of the leader device is different from the frame of reference of the proxy and the virtual follower device. Note that, although the examples presented in FIGS. 6A-6E are described using poses having two positional DOFs constrained according to the proxy constraint of FIG. 5C, the same issues described in the context of FIGS. 6A-6E may be present for poses having one DOF or three or more DOFs and/or proxy constraints of different types, such as any of the proxy constraints of FIGS. 5A-5L and/or other proxy constraints. Further, the same issues described in the context of FIGS. 6A-6E may be present for poses having positional and/or orientation DOFs in any quantity and in any combination.

As described herein, the frame of reference for the leader device is different from the frame of reference of the proxy and of the virtual follower device shown in FIGS. 6A-6E. Further, note that, although the examples presented in FIGS. 6A-6E are described using poses having two positional DOFs, the same issues described in the context of FIGS. 6A-6E may be present for poses having one DOF or three or more DOFs. Further, the same issues described in the context of FIGS. 6A-6E may be present for poses having positional and/or orientation DOFs in any quantity and in any combination, such as any of the proxy constraints described in conjunction with FIGS. 5A-5L.

As shown in FIG. 6A, under certain conditions, the virtual follower device 604(0) is able to accurately and quickly track the motion of the virtual leader device 602(0), where the motion of the virtual leader device 602(1) is based on the motion of the leader device. As a result, the pose of the virtual follower device 604(0), in the frame of reference of the virtual follower device 604(0), is coincident with the pose of the virtual leader device 602(0), in the frame of reference of the virtual leader device 602(0). When the operator 298 moves the virtual leader device 602(0) in the frame of reference of the virtual leader device 602(0), the virtual follower device 604(0) moves, in the frame of reference of the virtual follower device 604(0), in response such that the pose of the virtual follower device 604(0) remains coincident with the pose of the virtual leader device 602(0). For example, if the operator 298 moves the virtual leader device 602(0) to the left in the frame of reference of the virtual leader device 602(0), as shown in FIG. 6A, the virtual follower device 604(0) also moves left in the frame of reference of the virtual follower device 604(0) in response. As a result, the pose of the virtual follower device 604(0) and the pose of the virtual leader device 602(0) remain coincident with one another. Under such conditions, the processor does not generate a proxy constraint, and the virtual follower device 604(0) follows the commanded motion of the virtual leader device 602(0).

As shown in FIG. 6B, the operator 298 moves the virtual leader device 602(1) to the left in the frame of reference of the virtual leader device 602(1), and the virtual follower device 604(1) moves to the left in the frame of reference of the virtual follower device 604(1) in response. In this case, although the virtual follower device 604(1) moves in the same direction as the virtual leader device 602(1), the movement of the virtual follower device 604(1) lags behind the movement of the virtual leader device 602(1). As a result, the pose of the virtual follower device 604(1) is not coincident with the pose of the virtual leader device 602(1). This phenomenon can result from one or more source causes. As described herein, these source causes can include motion limits, velocity limits, acceleration limits, singularities, and/or the like. When the virtual follower device 604(1) and/or the associated functional structure approaches one or more of these limits, the processor generates a proxy 606(1). The proxy 606(1) serves as a virtual leader device 602(1) for the virtual follower device 604(1) to follow. When no proxy 606(1) is present, the virtual follower device 604(1) follows the commanded motion of the virtual leader device 602(1), as shown in FIG. 6A. However, when the proxy 606(1) is used, the virtual follower device 604(1) instead follows the commanded motion of the proxy 606(1).

The proxy 606(1) moves in the frame of reference of the proxy 606(1) in the same direction as the virtual leader device 602(1). The proxy 606(1) is positioned and/or oriented relative to the virtual follower device 604(1) such that the virtual follower device 604(1), when moving towards the pose of the proxy 606(1), moves in the same direction as the virtual leader device 602(1). Because the virtual leader device 602(1) is moving to the left in the frame of reference of the virtual leader device 602(1), the proxy 606(1) also moves to the left in the frame of reference of the proxy 606(1) and is posed to the left of the virtual follower device 604(1). As the virtual follower device 604(1) moves towards the proxy 606(1), the virtual follower device 604(1) moves to the left in the frame of reference of the virtual follower device 604(1), as well. In addition to generating the proxy 606(1), the processor further generates a proxy constraint 608(1) that constrains the movement of the proxy 606(1). As a result, the proxy 606(1) stays within the bounds of the proxy constraint 608(1).

As shown in FIG. 6C, when the operator 298 moves the virtual leader device 602(2) to the right in the frame of reference of the virtual leader device 602(2), the processor moves the proxy 606(2) in the frame of reference of the proxy 606(2) to place the proxy 606(2) to the right of the virtual follower device 604(2) and within the proxy constraint 608(2). As a result, the virtual follower device 604(2) moves to the right in the frame of reference of the virtual follower device 604(2) towards the pose of the proxy 606(2). Because the virtual follower device 604(2) moves the same direction as the virtual leader device 602(2), the motion of the virtual follower device 604(2) is intuitive to the operator 298 of the virtual leader device 602(2).

As shown in FIG. 6D, when the operator 298 moves the virtual leader device 602(3) upwards and to the right in the frame of reference of the virtual leader device 602(3), the processor moves the proxy 606(3) in the frame of reference of the proxy 606(3) to place the proxy 606(3) upwards and to the right of the virtual follower device 604(3) and within the proxy constraint 608(3). As a result, the virtual follower device 604(3) moves upwards and to the right in the frame of reference of the virtual follower device 604(3) towards the pose of the proxy 606(3). Because the virtual follower device 604(3) moves the same direction as the virtual leader device 602(3), the motion of the virtual follower device 604(3) is intuitive to the operator 298 of the virtual leader device 602(3).

As shown in FIG. 6E, when the operator 298 stops moving the virtual leader device 602(4), the processor moves the proxy 606(4) in the frame of reference of the proxy 606(4) to place the proxy 606(4) in the same pose as the virtual follower device 604(4) and within the proxy constraint 608(4). As a result, the virtual follower device 604(4) stops moving, because the virtual follower device 604(4) is in the same pose as the proxy 606(4). Because the virtual follower device 604(4) stops moving when the virtual leader device 602(4) stops moving, the behavior of the virtual follower device 604(4) is intuitive to the operator 298 of the virtual leader device 602(4).

Returning to FIG. 4, at a process 410, the processor determines the pose of the virtual follower device based on the pose of the proxy determined at process 408. In some embodiments, the pose of the virtual follower device is a function of a previous pose of the virtual follower device, the velocity of the virtual follower device, and/or the velocity of the proxy, as expressed in Equations 3-5 and 5B. In some examples, the movement of the virtual follower device does not fully correspond to the movement of the virtual leader device, due to the movement of the proxy within the proxy constraint. In such examples, the "excess" motion of the virtual leader device that the virtual follower device is unable to perform is smoothly discarded or "clutched away." Further, in some examples, the processor updates the proxy constraint based on the updated pose of the virtual follower device. Once the pose of the proxy is determined, the virtual follower device follows the pose of the proxy rather than the pose of the virtual leader device. The processor moves the pose of the virtual follower device based on the pose of the proxy.

At a process 412, the processor causes the functional structure to move based on the pose and/or motion of the virtual follower device. To accomplish such pose and/or movement, the functional structure can include various movable joints, links, and/or the like to effect the movement of the functional structure. The joints and links can be used to position the functional structure. The functional structure is used to teleoperatively move various instruments to follow the movement of the virtual follower device. Actuation of the degrees of freedom provided by joints of the instruments can be provided by actuators disposed in, or whose motive force (e.g., linear force or rotary torque) is transmitted to, the instruments. Accordingly, the degrees of freedom of the instruments can be controlled by actuators that drive the functional structure in accordance with control signals determined based on the pose and/or motion of the virtual follower device. The control signals can be determined to cause instrument motion or other actuation as indicated by movement of the virtual follower device and/or any other control signal.

The techniques described herein can be applied to various types of functional structures. In some examples, a portion of a functional structure corresponding to a virtual follower device with limited degrees of freedom can include a stapling instrument without an articulated wrist or joggle joints, such as can be available in certain other instruments. Such instruments with limited degrees of freedom can rely on the degrees of freedom of other portions of the functional structure for repositioning. In some examples, multiple instruments are supported by a same functional structure where one instrument has fewer degrees of freedom than another instrument (e.g., a stapler instrument without a joint along a shaft and a different instrument with one or more joints along the shaft). As a result, movement of one of the instruments relies on the degrees of freedom of the functional structure to follow the motion of the virtual follower device. Further, movement of the functional structure can cause one instrument to move, where, in order to cause another instrument to remain still, the manipulable joints of the other instrument move in a manner that counteracts the movement of the functional structure due to the rigid instrument. Additionally or alternatively, in order to cause another instrument to move, the movement of the manipulable joints of the other instrument is a composite of the motion for that other instrument with motion that counteracts the movement of the functional structure due to the rigid instrument. Techniques for manipulating multiple instruments in a teleoperative system are described more fully in U.S. Provisional Patent Application No. 63/071,971 (filed Aug. 28, 2020), entitled, "METHOD AND SYSTEM FOR COORDINATED MULTIPLE-TOOL MOVEMENT USING A DRIVABLE ASSEMBLY" which is incorporated herein by reference.

The method 400 then returns to process 402, described above, so that the processor can receive additional movement commands from an input device, such as by detecting motion of one or more input devices in response to being manipulated by the operator 298.

In some examples, the teleoperative system provides one or more feedback modalities to the operator 298 in order to inform the operator 298 about the existence and/or behavior of the proxy. In that regard, the teleoperative system can generate operator feedback when a proxy and/or proxy constraint is generated. Additionally or alternatively, the teleoperative system can generate operator feedback when motion of the input device is being clutched away by the functional structure. The feedback can be in the form of haptic feedback to one or more components of the input device. In some examples, the intensity of the haptic feedback can vary based on a difference between the pose of the proxy and the corresponding pose of the virtual follower device. Additionally or alternatively, the feedback can be in the form of visual feedback to a display of the user input system. Additionally or alternatively, the feedback can be in the form of audible feedback to a speaker or other audio device of the user input system.

Advantageously, the movement of the proxy is responsive to the movement of the virtual leader device but constrained in at least one degree of freedom based on a pose of the virtual follower device. The virtual follower device moves towards the proxy rather than towards the virtual leader device. As a result, the risk of uncontrolled, unexpected, or undesirable motion is reduced. The proxy constraint can be defined such that movement of the functional structure is more intuitive even as the virtual follower device approaches a motion limit (e.g., a range of motion limit, an acceleration limit, a velocity limit, a singularity, and/or the like). Therefore, the proxy can be used as a risk mitigation in a safety critical workspace.

As discussed above and further emphasized here, FIG. 4 is merely an example which should not unduly limit the scope of the claims. One of ordinary skill in the art would recognize many variations, alternatives, and modifications. In some embodiments, when more than one functional structure and/or virtual follower device is used, separate proxies can be introduced based on limits for each of the various functional structures and/or virtual follower devices during various instances and/or version of method 400. In such embodiments, each of the functional structures and/or virtual follower devices may apply different proxy constraints independently of one another and/or in conjunction with one another.

In some examples, the virtual leader device and the virtual follower device are optional and can be omitted. In such examples, the pose of the proxy is determined directly from the input device, and the proxy directly controls the functional structure. The flow diagram shown in FIG. 4 would change as follows. Process 404 is omitted. At process 406, the processor determines a proxy constraint based on a limitation and/or a pose of the functional structure. At process 408, the processor determines the pose of the proxy based on motion of the input device from the command received in process 402. At process 410, the processor determines the pose of the functional structure and, at process 412, causes the functional structure to move accordingly.

Some examples of control units, such as the control unit 140 of FIG. 1 can include non-transient, tangible, machine-readable media that include executable code that when executed by one or more processors (e.g., the processor 150 of FIG. 1) can cause the one or more processors to perform the processes of method 400. Some common forms of machine-readable media that may include the processes of method 400 are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

What is claimed is:

1. A computer-assisted device comprising:
an input control;
a functional structure configured to include a repositionable structure, the repositionable structure configured to support an instrument; and a processing system configured to:

receive a movement command from the input control, update a pose of a proxy based on the movement command and a proxy constraint, wherein the proxy constraint limits possible poses of the proxy relative to a virtualized repositionable structure, and cause the functional structure to move based on the updated pose of the proxy.

2. The computer-assisted device of claim 1, wherein the proxy constraint limits the possible poses of the proxy by: defining a maximum allowable distance between the updated pose of the proxy and a corresponding pose of the functional structure in at least one degree of freedom.

3. The computer-assisted device of claim 2, wherein the maximum allowable distance is based on an extent to which motion of the functional structure is limited.

4. The computer-assisted device of claim 2, wherein the maximum allowable distance is based on a distance between the pose of the functional structure and a region where the functional structure has a reduced ability to move.

5. The computer-assisted device of claim 1, wherein the proxy constraint limits the possible poses of the proxy by:

constraining the updated pose of the proxy relative to a corresponding pose of the functional structure along a first degree of freedom; and not constraining the updated pose of the proxy relative to the corresponding pose of the functional structure along a second degree of freedom.

6. The computer-assisted device of claim 1, wherein the proxy constraint is defined further based on a pose of the functional structure.

7. The computer-assisted device of claim 6, wherein the proxy constraint being defined further based on the pose of the functional structure comprises: a size or a shape of the proxy constraint being defined based on the pose of the functional structure.

8. The computer-assisted device of claim 1, wherein to update the pose of the proxy, the processing system is configured to determine a pose of the proxy based on a function of a previous pose of the functional structure and a constraint term.

9. The computer-assisted device of claim 8, wherein the constraint term is a function of a difference between an unconstrained pose of the proxy and the previous pose of the functional structure.

10. The computer-assisted device of claim 1, wherein the proxy constraint constrains the pose of the proxy along a first degree of freedom and along a second degree of freedom.

11. The computer-assisted device of claim 10, wherein the proxy constraint constrains the pose of the proxy equally along the first degree of freedom and the second degree of freedom.

12. The computer-assisted device of claim 1, wherein to cause the functional structure to move based on the updated pose of the proxy, the processing system configured to:

update a pose of a virtual follower device in virtual space based on the updated pose of the proxy; and cause the functional structure to move in physical space based on the pose of the virtual follower device in virtual space.

13. The computer-assisted device of claim 1, wherein the proxy constraint is defined based on a pose of a follower device.

14. A method comprising:

receiving, by a processing system, a movement command from an input control of a computer-assisted device, updating, by the processing system, a pose of a proxy based on the movement command and a proxy constraint, wherein the proxy constraint limits possible poses of the proxy relative to a virtualized functional structure, and causing, by the processing system, a functional structure of the computer-assisted device to move based on the updated pose of the proxy.

15. The method of claim 14, wherein the proxy constraint limits the possible poses of the proxy by: defining a maximum allowable distance between the updated pose of the proxy and a corresponding pose of the functional structure in at least one degree of freedom.

16. The method of claim 15, wherein the maximum allowable distance is based on:

an extent to which motion of the functional structure is limited; or a distance between the pose of the functional structure and a region where the functional structure has a reduced ability to move.

17. The method of claim 14, wherein the proxy constraint limits the possible poses of the proxy by:

constraining the updated pose of the proxy relative to a corresponding pose of the functional structure along a first degree of freedom; and not constraining the updated pose of the proxy relative to the corresponding pose of the functional structure along a second degree of freedom.

18. The method of claim 14, wherein:

the proxy constraint is defined further based on a pose of the functional structure; and the pose of the functional structure comprises: a size or a shape of the proxy constraint being defined based on the pose of the functional structure.

19. The method of claim 14, wherein causing the functional structure to move based on the updated pose of the proxy comprises:

updating a pose of a virtual follower device in virtual space based on the updated pose of the proxy; and causing the functional structure to move in physical space based on the pose of the virtual follower device in virtual space.

20. One or more non-transitory machine-readable media comprising a plurality of machine-readable instructions which when executed by one or more processors associated with a computer-assisted device are adapted to cause the one or more processors to perform a method comprising:

receiving a movement command from an input control of a computer-assisted device, updating a pose of a proxy based on the movement command and a proxy constraint, wherein the proxy constraint limits possible poses of the proxy relative to a virtualized functional structure, and causing a functional structure of the computer-assisted device to move based on the updated pose of the proxy.

* * * * *